United States Patent [19]
Junino et al.

[11] Patent Number: 5,807,540
[45] Date of Patent: Sep. 15, 1998

[54] NAIL VARNISH COMPOSITION COMPRISING A CROSSLINKED POLYESTER

[75] Inventors: Alex Junino, Livry Gargan; Roland Ramin, Itteville, both of France

[73] Assignee: L'Oreal, Paris, France

[21] Appl. No.: 643,352

[22] Filed: May 6, 1996

[30] Foreign Application Priority Data

May 5, 1995 [FR] France .................................. 95 05421

[51] Int. Cl.⁶ ..................................... A61K 7/04
[52] U.S. Cl. .............................. 424/61; 424/401
[58] Field of Search ................. 424/61, 63, 401

[56] References Cited

U.S. PATENT DOCUMENTS 3,925,295 12/1975 Osborn et al. .................. 260/34.2
5,165,915 11/1992 Tokubo et al. .............................. 424/63
5,580,548 12/1996 Mellul et al. .............................. 424/61

FOREIGN PATENT DOCUMENTS

D6445865 9/1965 Australia .

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

A cosmetic composition, in particular a nail varnish, comprising a crosslinked polyester as plasticizer.

The crosslinked polyester may be derived from the polycondensation of adipic acid, diethylene glycol and a polyol having at least three hydroxyl groups.

22 Claims, No Drawings

NAIL VARNISH COMPOSITION COMPRISING A CROSSLINKED POLYESTER

The present invention relates to a coloured or colourless nail varnish composition comprising a crosslinked polyester as plasticizer.

Among the main characteristics which nail varnishes must possess, mention must be made of the absence of irritation of the skin and the nails, good application, the production of a uniform film of excellent sheen and a rapid drying time for the film, as well as good adhesion to the surface of the nail, a certain amount of flexibility and good film strength so as to avoid cracking and flaking of the film. These characteristics are generally referred to as cosmetic characteristics.

In general, at the present time, film-forming materials such as nitrocellulose associated, if necessary, with another polymer such as an acrylic resin or an alkyd resin, and with plasticizers are used to impart good adhesion and good flexibility of the film (see FR-A-2,679,445).

The plasticizers commonly used are plasticizers of phthalate type such as dibutyl phthalate, of citrate type such as acetyl citrate, of glycol ester type such as the ester of neopentyl glycol or of propylene glycol, of glyceryl benzoate type and, lastly, camphor.

These plasticizers make it possible to adjust the flexibility of the film without weakening its physical strength.

Presently, however, it is desired to use plasticizers other than phthalates in the varnishes, since phthalates may be involved in allergies, and also other than camphor whose volatility does not allow the composition to have constant varnish characteristics while at the same time preserving adequate cosmetic characteristics.

Applicant has found, surprisingly, that it is possible to use a crosslinked polyester as plasticizer in nail varnish compositions with an organic medium, without modifying the cosmetic properties of the varnish and while at the same time obtaining a stable composition, as well as a flexible and shiny film.

More precisely, the invention relates to a cosmetic composition, in particular a nail varnish, comprising at least one film-forming material, at least one plasticizer and a solvent medium, wherein the plasticizer comprises at least one crosslinked polyester derived from the polycondensation of adipic acid, diethylene glycol and a polyol having at least three hydroxyl groups.

Preferably, the polyol of the crosslinked polyester contains three hydroxyl groups, such as glycerol.

As a crosslinked polyester of adipic acid, diethylene glycol and glycerol, mention may be made in particular of the polyester marketed under the reference "Lexorez 100" by the company Inolex.

The crosslinked polyester may preferably be present in the composition according to the invention in a content ranging from 0.1% to 15% by weight relative to the total weight of the composition.

The crosslinked polyester may be used alone or combined with another plasticizer known to those skilled in the art.

The plasticizers which may be used in combination with the crosslinked polyester may be chosen, for example, from those mentioned in FR-A-2,679,445, such as dibutyl, dioctyl, diisobutyl and dimethoxyethyl phthalates; benzyl and glyceryl benzoates; triethyl and tributyl citrates, tributyl acetyl citrate; tributyl and triphenyl phosphates; glycols and camphor, as well as derivatives and mixtures thereof. Preferably these plasticizers do not represent more than 50% by weight of the total amount of plasticizer.

The film-forming materials according to the invention comprise any film-forming material known to those skilled in the art and, in particular, nitrocellulose optionally combined with an alkyd resin, a polyester resin, an acrylic resin, a polyurethane resin, a polyamide resin, a vinyl resin and, in general, with any resin compatible with the medium. These resins make it possible to increase the film-forming power of nitrocellulose and improve the sheen as well as the adhesion of the films.

It is moreover possible to replace, totally or partially, nitrocellulose by a polyvinyl resin such as polyvinyl butyral or by cellulose acetobutyrate.

It has furthermore been observed that when the composition according to the invention comprises a crosslinked polyester according to the invention as sole plasticizer and nitrocellulose as film-forming material, a coatable film is obtained after application to the nail.

According to the invention, the solvent medium may essentially consist of a mixture of various volatile organic solvents, in order to obtain relatively short drying times.

The solvents used are preferably compatible with the resins used so as to ensure that they dissolve. Among these solvents, which are those conventionally used in nail varnishes, mention may be made of ketones such as acetone, methyl ethyl ketone and methyl isobutyl ketone; glycol ethers; alcohols such as ethanol, n-butanol, n-propanol and isopropanol; acetates such as butyl acetate, ethyl acetate, isopropyl acetate and 2-methoxyethyl acetate; linear or branched hydrocarbons such as hexane or octane; or alternatively aromatic hydrocarbons such as xylene and toluene.

In a preferred embodiment, the composition according to the invention comprises in particular, by weight, from 0.1 to 15% of plasticizer, from 5 to 35% of film-forming material and from 50 to 94.9% of solvent medium, relative to the total weight of the composition.

When the nail varnish according to the invention is a coloured varnish, at least one pigment of organic or inorganic nature, a dye, a lake and/or a pearlescent agent well known to those skilled in the art may be incorporated therein.

Moreover, in order to avoid sedimentation of the pigments, certain thixotropic rheological agents may be employed, such as clays of the bentonite, hectorite or montmorillonite type. These agents also serve as thickeners.

The compositions according to the invention may moreover contain adjuvants commonly used in nail varnishes. Among these adjuvants which may be mentioned are UV screening agents such as benzophenone derivatives and ethyl 2-cyano-3,3-diphenyl acrylate, silicones and fluoro agents.

Obviously, a person skilled in the art will take care to select these possible additional compounds and/or the amount thereof, such that the advantageous properties of the composition according to the invention are not, or substantially not, adversely affected by the addition envisaged.

Another subject of the invention is the use of a crosslinked polyester as defined above as plasticizer in a cosmetic composition, in particular a nail varnish, comprising at least one film-forming material and at least one solvent medium.

Several examples of nail varnish compositions according to the invention will now be given by way of illustration and with no limiting nature.

EXAMPLE 1

A colourless nail varnish is prepared, having the following composition:

| | |
|---|---|
| Nitrocellulose | 20 g |
| Crosslinked polyester (Lexorez 100 from the company Inolex) | 8 g |
| Bentonite | 1 g |
| Additives | 0.5 g |
| Solvent (ethyl acetate, butyl acetate) | qs 100 g |

The varnish spreads easily and, after drying, gives a flexible and shiny film.

EXAMPLE 2

A colourless nail varnish is prepared, having the following composition:

| | |
|---|---|
| Nitrocellulose | 15 g |
| Crosslinked polyester (Lexorez 100 from the company Inolex) | 6 g |
| Bentone | 1 g |
| Additives | 3.5 g |
| Tosylamide/formaldehyde resin | 12 g |
| Solvent (ethyl acetate, butyl acetate) | qs 100 g |

The varnish spreads easily and, after drying, gives a flexible and shiny film.

EXAMPLE 3

A colourless nail varnish is prepared, having the following composition:

| | |
|---|---|
| Nitrocellulose | 15 g |
| Crosslinked polyester (Lexorez 100 from the company Inolex) | 8 g |
| Bentone | 1 g |
| Additives | 1 g |
| Tributyl acetyl citrate | 6 g |
| Solvents (ethyl acetate, butyl acetate) | qs 100 g |

The varnish spreads easily and, after drying, gives a flexible and shiny film.

We claim:

1. A cosmetic composition comprising from 5 to 35% of at least one film-forming material, from 0.1 to 15% at least one plasticizer and from 50 to 94.9% of a solvent medium, wherein said plasticizer comprises at least one crosslinked polyester derived from the polycondensation of adipic acid, diethylene glycol and a polyol having at least three hydroxyl groups.

2. A composition according to claim 1 wherein said polyol contains three hydroxyl groups.

3. A composition according to claim 1 wherein said polyol is glycerol.

4. A composition according claim 1 wherein said crosslinked polyester is present in the composition in an amount ranging from 0.1% to 15% by weight relative to the total weight of the composition.

5. A composition according to claim 1 wherein said crosslinked polyester is combined with at least one other plasticizer, wherein said other plasticizer is not a crosslinked polyester derived from the polycondensation of adipic acid, diethylene glycol and a polyol having at least three hydroxyl groups.

6. A composition according to claim 5 wherein said at least one other plasticizer is dibutyl phthalate, dioctyl phthalate, diisobutyl phthalate, dimethoxyethyl phthalate, benzyl benzoate, glyceryl benzoate, triethyl citrate, tributyl citrate, tributyl acetyl citrate, tributyl phosphate, triphenyl phosphate, a glycol, or camphor.

7. A composition according to claim 5 wherein said other plasticizer is present in an amount ranging up to 50% by weight relative to the total amount of plasticizer.

8. A composition according to claim 1 wherein said film-forming material is nitrocellulose, polyvinyl butyral, or cellulose acetobutyrate.

9. A composition according to claim 8 wherein said film-forming material further comprises a resin compatible with the solvent medium.

10. A composition according to claim 9 wherein said resin compatible with the solvent medium is an alkyd resin, a polyester resin, an acrylic resin, a polyurethane resin, a polyamide resin, or a vinyl resin.

11. A composition according to claim 1 wherein said solvent medium comprises a mixture of volatile organic solvents.

12. A composition according to claim 11 wherein said volatile organic solvents are ketones, glycol ethers, alcohols, acetates, linear or branched hydrocarbons, or aromatic hydrocarbons.

13. A composition according to claim 12 wherein said ketones are acetone, methyl ethyl ketone or methyl isobutyl ketone; wherein said alcohols are ethanol, n-butanol, n-propanol, or isopropanol; wherein said acetates are butyl acetate, ethyl acetate, isopropyl acetate, or 2-methoxyethyl acetate; wherein said linear or branched hydrocarbons are hexane or octane; and wherein said aromatic hydrocarbons are xylene or toluene.

14. A composition according to claim 1 wherein said composition is in the form of a nail varnish.

15. A composition according to claim 14 wherein said nail varnish is a colored varnish.

16. A composition according to claim 15 wherein said colored varnish comprises at least one coloring agent, wherein said at least one coloring agent is an organic pigment, an inorganic pigment, a dye, a lake, or a pearlescent agent.

17. A composition according to claim 15 wherein said colored varnish further comprises at least one thixotropic rheological agents.

18. A composition according to claim 17 wherein said thixotropic rheological agent is a bentonite clay, a hectorite clay or a montmorillonite clay.

19. A method of plasticizing a cosmetic composition containing at least one film-forming material and at least one solvent medium, said method comprising preparing a cosmetic composition containing as a plasticizer a crosslinked polyester derived from the polycondensation of adipic acid, diethylene glycol and a polyol having at least three hydroxyl groups.

20. A method according to claim 19 wherein said polyol contains three hydroxyl groups.

21. A method according to claim 20 wherein said polyol is glycerol.

22. A method according to claim 19 wherein said cosmetic composition is a nail varnish composition.

* * * * *

UNITED STATES PATENT AND TRADEMARK OFFICE
CERTIFICATE OF CORRECTION

PATENT NO.: 5,807,540

DATED: September 15, 1998

INVENTOR(S): Alex JUNINO and Roland RAMIN

It is certified that an error appears in the above-identified patent and that said Letters Patent is hereby corrected as shown below:

IN THE CLAIMS:

Claim 1, Col. 3, line 43, after "15%", insert --of--.

Claim 4, Col. 3, line 53, after "according", insert --to--.

Signed and Sealed this

Fifteenth Day of December, 1998

Attest:

BRUCE LEHMAN

Attesting Officer

Commissioner of Patents and Trademarks